US011013251B2

(12) United States Patent
Dai et al.

(10) Patent No.: US 11,013,251 B2
(45) Date of Patent: May 25, 2021

(54) EMBEDDED LIQUID LUBRICANTS FOR TABLETING

(71) Applicant: PF CONSUMER HEALTHCARE 1 LLC, Wilmington, DE (US)

(72) Inventors: Yong Dai, Mechanicsville, VA (US); Alan M. Goldberg, Nutley, NJ (US); Michael A. Goode, Powhatan, VA (US); Raymond Alan Bartolucci, Poughkeepsie, NY (US); James O. Frazier, Powhatan, VA (US)

(73) Assignee: PF Consumer Healthcare 1, LLC, Wilmington, DE (US)

( * ) Notice: Subject to any disclaimer, the term of this patent is extended or adjusted under 35 U.S.C. 154(b) by 0 days.

(21) Appl. No.: 15/601,114

(22) Filed: May 22, 2017

(65) Prior Publication Data
US 2017/0251711 A1 Sep. 7, 2017

Related U.S. Application Data

(63) Continuation of application No. 14/449,335, filed on Aug. 1, 2014, now abandoned, which is a continuation of application No. 11/787,381, filed on Apr. 16, 2007.

(51) Int. Cl.

| | | |
|---|---|---|
| A23L 33/15 | (2016.01) | |
| A23P 10/25 | (2016.01) | |
| A23P 10/28 | (2016.01) | |
| A23L 29/00 | (2016.01) | |
| A23L 29/10 | (2016.01) | |
| A23L 33/00 | (2016.01) | |
| A23L 33/10 | (2016.01) | |
| A23L 33/115 | (2016.01) | |
| A23L 33/16 | (2016.01) | |
| A61K 9/20 | (2006.01) | |

(52) U.S. Cl.
CPC ............ *A23L 33/15* (2016.08); *A23L 29/035* (2016.08); *A23L 29/10* (2016.08); *A23L 33/10* (2016.08); *A23L 33/115* (2016.08); *A23L 33/16* (2016.08); *A23L 33/40* (2016.08); *A23P 10/25* (2016.08); *A23P 10/28* (2016.08); *A61K 9/2095* (2013.01); *A23V 2002/00* (2013.01)

(58) Field of Classification Search
CPC ........ A61K 9/2866; A23L 33/16; A23P 10/28

USPC .............................. 426/72, 73, 74, 601, 519
See application file for complete search history.

(56) References Cited

U.S. PATENT DOCUMENTS

| | | | |
|---|---|---|---|
| 3,518,343 | A | 6/1970 | Welsh et al. |
| 3,518,344 | A | 6/1970 | Welsh et al. |
| 3,518,345 | A | 6/1970 | Dines et al. |
| 3,577,490 | A * | 5/1971 | Welsh et al. |
| 3,577,492 | A | 5/1971 | Welsh et al. |
| 3,619,292 | A | 11/1971 | Brouillard et al. |
| 3,619,462 | A | 11/1971 | Dines et al. |
| 3,655,852 | A * | 4/1972 | Koff et al. |
| 4,603,143 | A | 7/1986 | Schmidt |
| 5,922,351 | A | 4/1999 | Daher |
| 6,162,474 | A | 12/2000 | Chen et al. |
| 6,254,886 | B1 * | 7/2001 | Fusca et al. |
| 6,638,557 | B2 * | 10/2003 | Qi et al. |
| 2001/0009679 | A1 | 7/2001 | Chen et al. |
| 2002/0172721 | A1 * | 11/2002 | Boulos et al. |
| 2006/0135446 | A1 * | 6/2006 | Takagaki et al. |

FOREIGN PATENT DOCUMENTS

| | | |
|---|---|---|
| EP | 0062225 A | 10/1982 |
| GB | 1422974 A | 1/1976 |
| GB | 2142824 A | 1/1985 |
| JP | 2000178206 A | 6/2000 |
| JP | 2002188095 A | 7/2002 |
| WO | 9104018 A1 | 4/1991 |

OTHER PUBLICATIONS

Hiroyuki Aoshima, et al., Glycerin Fatty Acid Esters as a New Lubricant of Tablets, International Journal of Pharmaceutics, 293, pp. 25-34 (2005).

Database WPI Week 197728, Thomson Scientific, London, GB; AN 1977-49626Y XP002492710 & JP 52 066615 A (Sawai Seiyaku KK) Jun. 2, 1977 (Jun. 2, 1977) abstract.

\* cited by examiner

*Primary Examiner* — Helen F Heggestad
(74) *Attorney, Agent, or Firm* — Roshni A. Sitapara

(57) ABSTRACT

The invention provides a nutritional supplement and/or pharmaceutical composition for tableting comprising an embedded lubrication matrix. The embedded lubrication matrix comprises an oily liquid finely dispersed in an oil insoluble material. A method of lubricating a nutritional supplement or pharmaceutical composition for tableting using a matrix with embedded lubrication is also provided.

16 Claims, No Drawings

EMBEDDED LIQUID LUBRICANTS FOR TABLETING

The present application is a continuation application of abandoned U.S. patent application Ser. No. 14/449,335 filed Aug. 1, 2014, which is a continuation application of copending U.S. patent application Ser. No. 11/787,381 filed Apr. 16, 2007, which is entitled "Embedded Liquid Lubricants for Tableting," the contents of which are incorporated herein in their entirety to the extent that is consistent with this invention and application.

FIELD OF INVENTION

This invention relates to pharmaceutical and nutriceutical tablets. More particularly the invention provides a composition and method for effective lubrication in tableting.

BACKGROUND OF THE INVENTION

Stearic acid or metallic salts of stearic acid, particularly magnesium stearate, are commonly used as an excipient in pharmaceutical and nutriceutical compositions to facilitate the tableting process. Compounds such as magnesium stearate function as a lubricant and facilitate tableting by reducing friction at the tablet-die wall interface during tablet formation and ejection, and/or by preventing sticking to punch faces and the die wall.

Although used throughout the pharmaceutical and nutriceutical industry as a lubricant, use of magnesium stearate as a lubricant does have several disadvantages. Magnesium stearate is a laminar lubricant. As a laminar lubricant the structure of magnesium stearate is a stack of laminar sheets. Lubrication occurs when one or more laminar sheets are "peeled off" the stack and at least partially coat surrounding particles. Mixing facilitates removal of sheets from the stack and accordingly the degree of lubrication (i.e. lubrication with a laminar lubricant is "mixing sensitive").

As a composition comprising magnesium stearate is mixed, the laminar sheets peel off from the stack structure of magnesium stearate and coat the surrounding particles or granules of the composition. Accordingly, the mixing time, speed and/or mixing method impact the lubricating efficacy of magnesium stearate. For example, if too many laminar sheets peel off from the stack structure of magnesium stearate in the mixing process over lubrication occurs. Namely, particles get over coated with laminar sheets which reduce interparticular bonding leading to poor compressibility and lower tablet hardness, thus creating potential processing problems and/or the propensity for malformed tablet. In some cases over lubrication can render the tablet hydrophobic which may lengthen disintegration time undesirably.

Mixing is necessary for content uniformity but even modest changes in mixing time, speed and/or mixing mechanism introduce variation of lubrication levels when magnesium stearate or other laminar lubricant is used as a lubricant which in turn leads to the associated compressibility and tableting problems. When used as a lubricant, magnesium stearate is typically added to the composition in a separate last step before tableting to provide control of the lubrication process and minimize the opportunity for over-lubrication or undesirable disruption of the magnesium stearate structure in the mixing process.

Conventionally liquid lubricants have not been particularly useful in powder blend compositions of nutriceuticals and/or pharmaceuticals intended for tableting. Typically, liquid lubricants can only be added in small quantities to powder blends and must be added immediately prior to compression because they tend to wet the powder blends rendering mixing difficult.

Two approaches to overcoming the problems associated with the use of liquid lubricants have been suggested. One approach is the conversion of liquid unsaturated vegetable oil lubricants into solid saturated oil lubricants by hydrogenation. This approach has the disadvantages that: (1) hydrogenated vegetable oils are associated with an increased risk of coronary heart disease, and (2) hydrogenated vegetable oils are not nearly as effective tableting lubricants as the common metal stearate lubricants.

A second approach used to facilitate use of liquid lubricants in dry mixtures intended for tableting was to coat liquid lubricants with an oil-insoluble film-forming substance to avoid the wetting issue. The film forming material assembles to form a layer or skin over the surface of an oil droplet. Film forming substances as set forth in U.S. Pat. No. 3,518,343 include water soluble gums such as gum Arabic, pectin, traganth, modified celluloses such as hydroxypropyl cellulose or carboxymethyl cellulose, alginates or proteinaceous material such as gelatin. While the oil insoluble film-former may address the wetting issue to some extent, the film-coated liquids known in the art have substantially decreased lubrication efficiency as the lubricant is encased in the film.

Accordingly a composition and/or method for improved lubrication of dry nutriceutical and/or pharmaceutical compositions for tableting is needed.

SUMMARY OF INVENTION

In one embodiment the invention provides a nutritional supplement tablet composition comprising an embedded lubrication matrix. The embedded lubrication matrix comprises an oily liquid finely dispersed in an oil insoluble material. In an exemplary embodiment the nutritional supplement composition is substantially free of stearate. Oily liquids suitable for dispersion in the oil insoluble material include, but are not limited to, Vitamin E, animal oil, synthetic oil, mineral oil, polyethylene glycol, silicon oil and combinations thereof. Suitable oil insoluble materials include, but are not limited to, starch, dextrin, microcrystalline cellulose, ethylcelulose, gelatin, sugars, glucose, maltose, fructose, sorbitol, sucrose, mannitol, sorbitol, lactose, methylcellulose, hydroxypropylmethyl cellulose, maltodextrin, silicon dioxide, anhydrous dicalcium phosphate, and combinations thereof.

The composition may be a direct compression, roller compaction or granulation composition.

One embodiment of the invention provides a pharmaceutical composition for tableting comprising an embedded lubrication matrix wherein the embedded lubrication matrix comprises an oily liquid dispersed in an oil insoluble base material, and wherein the pharmaceutical composition is substantially free of stearate.

A method of lubricating a nutritional supplement or pharmaceutical composition for tableting is provided. The method comprises providing a matrix with embedded liquid lubricant, providing a nutritional supplement composition or pharmaceutical composition, mixing the matrix with embedded liquid lubricant and the nutritional supplement or pharmaceutical composition, and forming a tablet. The nutritional supplement or pharmaceutical composition may be a direct compression mixture, a roller compaction mixture or comprise a granulation.

DETAILED DESCRIPTION OF INVENTION

The present invention provides a composition comprising a matrix with embedded liquid lubricants. The embedded liquid lubricants serve to provide lubrication for tableting of the composition. More particularly, the matrix with embedded liquid lubricant of the invention is an oil-insoluble-particulate-solid base material having a viscous oily liquid lubricant dispersed in the base material. In a preferred embodiment the matrix with embedded liquid lubricant may be used as an alternative to metal stearate lubricants such as magnesium stearate as a tableting lubricant for nutriceutical or pharmaceutical compositions. Alternatively the matrix with embedded lubricant may be used as a partial replacement for stearate lubricants or other tableting lubricants. The matrix with embedded lubricant is a useful lubricant for tableting dry nutritional and/or pharmaceutical compositions such as, for example, vitamin and/or mineral compositions. The matrix with embedded lubricant is particularly useful for compositions subjected to direct compression in the tableting process. In one exemplary embodiment, liquid Vitamin E acetate finely dispersed in a starch/dextrin matrix was found to effectively lubricate a multi-vitamin and mineral formulation for direct compression.

In addition to providing lubrication for tableting the compositions of the invention generally may offer one or more of the following advantages particularly as compared to the traditional metal stearate lubricants:
  (1) Elimination of the adverse impacts of magnesium stearate over-lubrication on compressibility;
  (2) More efficient manufacturing process by eliminating a separate lubricant addition and blending (e.g. mixing) stage;
  (3) Less lubricant induced softening effect on tablet hardness;
  (4) Lower friability of tablets;
  (5) Reduced prolongation of disintegration times at low concentrations; and/or
  (6) Good compatibility with other ingredients.

Embodiments having Vitamin E as the lubricant embedded in the matrix may provide the additional benefits of antioxidant activity and/or nutritional supplementation of Vitamin E.

The invention further includes a method of lubricating a nutritional or pharmaceutical composition for tableting by providing a matrix with embedded liquid lubricant, and a nutritional supplement or pharmaceutical composition, and mixing the matrix with embedded liquid lubricant with the nutritional supplement or pharmaceutical composition prior to tableting.

The inventors believe without wishing to be bound to the theory that embedding a liquid lubricant in a matrix allows the liquid lubricant to be evenly distributed in the matrix without wetting the matrix. Upon compression, the liquid lubricant may be extruded from the matrix and provide lubrication for tableting, eliminating the over-lubrication issues seen with stearic acid and metal stearates. Since the liquid lubricant in a matrix does not have mixing related over-lubrication issues, it can be added with other components for mixing in a single step. Thus, the conventional step of adding lubricant as a separate step immediately before tableting can be avoided.

As used herein the term "matrix with embedded liquid lubricants" means a composition comprising at least one oily liquid finely dispersed in an oil insoluble material wherein the matrix appears to be dry and no oil or oily appearance is visible to the human eye and the matrix is free flowing. Small particles of oil are incorporated in the mass of the oil insoluble material (e.g. interspersed in the interstitial spaces of the oil insoluble material.) The lubricant may be displaced from the matrix by the compression forces of the tableting process. The oil insoluble material may be a single component or mixture of components. Typically, the oil insoluble material is in the form of dry particles. Likewise, the oily liquid may be a single entity or a mixture of oily liquids. Each of the materials comprising the matrix with embedded liquid lubricants should be a material that is acceptable for consumption by a mammal.

As used herein the term "oil" means a substance that is substantially insoluble in water (as designated by the Merck Index, CRC Handbook or MSDS Data sheet) and that is a liquid at ambient temperatures. An "embedded liquid lubricant" includes oils as well as other materials which are liquids at ambient temperatures, have lubricating properties, and do not react with or solubilize the oil insoluble material.

Embedded liquid lubricants are distinguished from film-coated lubricants in that there is no chemical or physical process that causes the oil insoluble material to assemble a layer over the surface of an oil droplet. A simple listing of oil insoluble materials suitable for forming a matrix and a listing of film forming polymers may over lap; however, chemical identity alone is not dispositive. The method of combining, proportions used, the presence of other reactive entities, amount of moisture and temperature are exemplary of factors that may determine whether a film-coated oil is formed or a matrix with embedded lubricant is formed.

As used herein the term "stearate(s)" includes stearic acid and metallic salts of stearic acids. Magnesium stearate is an exemplary metallic salt of stearic acid. Substantially, free of stearates means that the composition comprises less than 0.01% stearate by weight.

The term "multivitamin and mineral" or "multivitamin and multimineral" supplement(s) includes compositions comprising, at least one vitamin and at least one mineral and optionally one or more related nutritional agent. The terms "multivitamin and mineral" or "multivitamin and multimineral" should be interpreted in a like manner herein when they proceed the terms "supplement", "tablet", or "composition". Additionally multivitamin and mineral supplement is an example of nutritional supplement and/or a nutriceutical.

As used herein "nutritional agents" include substances other than vitamins and minerals known to have health benefits. Nutritional agents include, but are not limited to, carotinoids (such as lutein, lycopene, zeaxanthin, astaxantin, and related xanthanins), fiber, phytosterols, glucosides, polyphenols, B complex related compounds (such as choline and inositol), omega-3 fatty acids, probiotics, glucosamine, herbals, amino acids and peptides.

As used herein, the phrase "disintegration time" means the amount of time it takes for a tablet dosage unit of a pharmaceutical composition or nutritional supplement to disintegrate under controlled laboratory conditions. One of ordinary skill in the art is familiar with methods and procedures for determination of disintegration times.

The term "dry pharmaceutical composition" refers to a composition that is presented as a dry material for compressing into a tablet dosage form. While the composition is dry at the time of compression into a tablet, processing steps that involve moisture are not precluded so long as the material is not overtly moist at the time it is presented for tableting.

As used herein the terms "pharmaceutical active(s)", "active(s)", "active agent(s)", "therapeutic agent(s)", "drug (s)" should be considered to be equivalent terms and taken to mean a substance used in the prevention, diagnosis, alleviation, treatment, or cure of disease or medical condition.

The composition of the invention may comprise any nutritional or pharmaceutical composition, which may be formed into a tablet dosage form. Compositions with a plurality of nutritional components and/or pharmaceutical actives are also within the scope of the invention. For example, for nutritional embodiments, the composition may comprise a single nutritional component, a select group of components (such as, for example, a group of nutrients directed to bone health), or a wide spectrum of nutritional components such as vitamins and minerals, and optionally, one or more nutritional agents (such as, for example, commercial multivitamin and mineral tablets or multivitamin and mineral tablets with one or more added nutritional agents.)

Suitable vitamins and related entities which may be included in the compositions of the invention include, but are not limited to, Vitamin C, Vitamin E, thiamin (Vitamin $B_1$), riboflavin (Vitamin $B_2$), niacin (Vitamin $B_3$), pyridoxine (Vitamin $B_6$), folic acid, cobalamins (Vitamin $B_{12}$), Pantothenic acid (Vitamin $B_5$), Biotin, Vitamin A (and Vitamin A precursors), Vitamin D, Vitamin K, and other B complex vitamins, and mixtures thereof.

Suitable minerals which may be included in the composition of the invention include, but are not limited to, iron, iodine, magnesium, zinc, selenium, copper, calcium, manganese, silicon, molybdenum, vanadium, boron, nickel, tin phosphorus, chromium, cobalt, chloride, potassium and combinations thereof. Mineral components of multivitamin-multimineral tablets are typically provided in salt form. The salt form used should be a pharmaceutically acceptable salt form.

A listing of vitamins and minerals and related agents that may be included in nutritional supplements and dosage amounts are set forth in established reference guides such as the United States Pharmacopeia National Formulary Official Compendium of Standards (i.e., the U.S.P. N.F. Official Compendium of Standards) or European Directive 90/496/EC including amendments which are incorporated herein by reference. Amounts of vitamins and minerals may vary in specific embodiments but should typically fall within the dosage amounts set forth in the U.S.P. N.F. Official Compendium of Standards or European Union Directive Nutritional agents which may be included in the composition of the invention include, but are not limited to, carotinoids (such as lutein, tycopene, zeaxanthin, astaxanthin, and related xanthins), B complex related compounds such as choline and inositol, for example, fiber, phytosterols, probiotics, glucosides, polyphenols, choline, omega-3 fatty acids, glucosamine, herbals, amino acids and peptides.

The compositions of the invention further comprise a matrix with embedded liquid lubricant. The matrix comprises a base material portion and an oily liquid. The base material portion is an oil insoluble material. Oil insoluble materials suitable for the base material portion include, but are not limited to, starch, dextrin, microcrystalline cellulose, ethylcelulose, gelatin, sugars, glucose, maltose, fructose, sorbitol, sucrose, mannitol, sorbitol, lactose, methylcellulose, hydroxypropylmethyl cellulose, maltodextrin, silicon dioxide, anhydrous dicalcium phosphate, and combinations thereof. Suitable oily liquids include, but are not limited to, Vitamin E, animal oil, synthetic oil, mineral oil, organic liquid with lubricating function, polyethylene glycol, silicon oil and combinations thereof. Optionally, for processing purposes it may be desirable to include a processing aid such as, for example, silicon dioxide. The base material should be in a substantially particulate state in the matrix such that interparticulate spaces (or interstitial spaces) are available for receiving the small particles or fine droplets of the lubricant.

To avoid wetting and provided for uniform embedding of the oily liquid in the base material, the oily liquid is finely dispersed in the base material. Dispersion of the oily liquid in the base material should be such that the matrix appears to be dry and no oil or oily appearance is visible to the human eye and the matrix is free flowing. The amount of oily liquid dispersed in the base material will typically be up to about 70% wt/wt oil to oil plus base material. Typically about 10% to about 55% wt/wt oil to oil plus base material is convenient for maintaining the properties of the matrix and providing optimized quantities of lubricant per amount of matrix used in the tableting composition. These amounts are representative and other amount may be likewise suitable with the specific amount being dependent on the nature of the base material and oily liquid used, flow properties, and/or degree of lubrication desired.

For example, the release of Vitamin E acetate from a starch maltodextrin base material under compression differs from the release of Vitamin E acetate from a starch gelatin base material under compression. While adjusting the ratio of oil to matrix base and/or adding processing aids such as silicon dioxide, for example, are exemplary of methods that may be used to modulate the flow properties.

If the matrix is to be used in a composition intended for direct compression, preferably at least 70% of the matrix will have particle sizes that fall in the range of about 20 mesh (850 microns) to about 200 mesh (75 microns) as measured by US standard sieves. Additionally, for direct compression, the matrix with embedded lubricant will preferably have a Carr compressibility Index value of about 5 to about 21.

Amounts of matrix used will depend on amount of lubrication needed which, in turn, is a function of the chemical and physical properties of activities and excipients in the composition. In an exemplary embodiment of a multivitamin and mineral supplement comprising a substantial portion of abrasive minerals amounts of lubricant as low as about 0.1% to about 1.5% wt/wt of a matrix which is 50% by weight of lubricant may provide sufficient lubrication, for example.

The dispersion of the oily liquid in the base material may be accomplished with mixing. Base material particle size, speed of mixing and mechanism of mixing are exemplary of parameters which may be modified to achieve the desired dispersion. For example, small base material particle size and high shear mixing may be used to create the fine dispersion in which the oil is not visible to the human eye. Other methods such as spray processes, for example may be likewise suitable to finely disperse the oily liquid in the base material. If the base material comprises one or more materials that may react or assemble to form films under certain conditions, the method selected for preparing the matrix with embedded lubricant should avoid processing steps and or addition of substances that would lead to film formation.

As described above a number of lubricating materials may be suitable for dispersing/embedding in the matrix with embedded lubricants. However, Vitamin E may have some advantages over other traditional lubricating oils. Most traditional lubricating oils contain trans fats, which are associated with an increased risk of coronary heart disease. On the contrary, Vitamin E has been suggested to also assists in healthy heart and blood vessels. Furthermore, Vitamin E is widely acknowledged as a powerful antioxidant. Vitamin E is used as a supplement to prevent the destructive impacts of free radicals in human. Also Vitamin E is widely used as a preservative in a variety of consumer goods to maintain quality and/or prevent undesirable reactions and extend shelf life. Vitamin E may be used in free form or in a derivitized form such as, for example, Vitamin E acetate.

The use of a matrix with embedded Vitamin E is widely applicable as a tableting lubricant. Such a matrix is well suited for use with in direct compression compositions For example, a matrix with embedded vitamin E can effectively lubricate a direct compression multi-vitamin/mineral formulation, which contains high levels of abrasive metal salts. Abrasive materials such as metal salts are believed to make lubrication difficult. The matrix with embedded Vitamin E can be an effective sole lubricant for the multi-vitamin/mineral formulation, or the matrix with embedded vitamin E may be employed in conjunction with another lubricant for various tabletable formulations. Although well suited for use with direct compression composition, a matrix with vitamin E embedded is also suitable for use in compression blends with less abrasive materials, compositions subjected to roller compaction or in granulation compositions subjected to tableting.

The compositions in accordance with the present invention are intended for oral administration in a solid form (i.e. tablet). Accordingly, in order to form a solid dosage form, the composition may further comprise excipients and/or processing aides in addition to vitamins and minerals. Exemplary excipients and processing aids, include but are not limited to, absorbents, diluents, flavorants, colorants, stabilizers, fillers, binders, disintegrants, glidants, antiadherents, sugar or film coating agents, preservatives, buffers, artificial sweeteners, natural sweeteners, dispersants, thickeners, solubilizing agents and the like or some combination thereof. In a preferred embodiment, stearic acid and/or metal stearate lubricants are not included as excipients.

The nutritional compositions of the invention may be prepared by combining the matrix with embedded lubricant with the vitamin(s) and/or mineral(s) and/or nutritional agent(s) intended for inclusion in the tablet dosage form and tableting excipients. As the matrix with embedded lubricant is not mixing sensitive, the timing and/or manner of a addition of the matrix with embedded lubricant is not critical. Accordingly, a special addition step or steps for addition of the lubricant and/or special mixing provisions for the lubricant are not required.

Once the matrix with embedded lubricant and other components of the tableting mixture are combined, the composition thus prepared may be fed into a tablet press and formed into tablets. The compression forces of the tablet press are sufficient to extrude lubricant from the matrix to permit lubrication.

The matrix with embedded lubricant is well suited for use with direct compression blends (e.g. compositions prepared for direct compression). However, a matrix with embedded lubricants may likewise be useful for lubrication of granulation blends intended for tableting or compositions prepared by roller compaction as the lubrication function is achieved as the composition is pressed into a tablet.

Compositions of pharmaceutical actives for tableting utilizing a matrix with embedded lubricant as a tableting lubricant may be prepared as described above for the nutritional compositions.

Example 1

In one exemplary embodiment of a matrix with embedded lubricant is Vitamin E acetate dispersed in a base material of equal parts of modified food starch and maltodextrin. The ratio of vitamin E to base material is about 50/50 by weight. Silicon dioxide may be included in the matrix as a processing aid. Typically the processing silicon dioxide processing aid would be included in an amount of about 0.2 to 2.5%. The vitamin E, starch, maltodextrin and processing aid (if used) should be mixed such that the oily viscous vitamin E is finely dispersed in the starch maltodextrin base material and no liquid or viscous material is visible to the human eye. Mixing may be accomplished using a high shear mixer or alternatively a spray system. The mixing method should yield a matrix in the form of a free flowing powder. Once prepared, the matrix with embedded lubricant may then be combined with the material to be tableted. This composition is representative of the many matrix compositions that are within the scope of the invention and is provided for illustrative purposes.

Example 2

An example of a nutritional supplement composition of an exemplary embodiment of the invention is provided in Table 1. This composition is representative of the many compositions that are within the scope of the invention and is provided for illustrative purposes. The exemplary composition of Table 1 is a multivitamin and mineral supplement. For Table 1 the matrix with embedded lubricant is vitamin E finely dispersed in a starch maltodextrin base (50% w/w) with silicon dioxide as a processing aid as described in Example 1. The amount of matrix with embedded lubricant was varied from 0.3% to 8.8% for the individual samples of the nutritional supplement composition and accordingly is listed as a range of amounts in Table 1. The matrix with embedded lubricant was the sole lubricant in the composition (e.g. no magnesium stearate or other tableting lubricant was added. The composition of the formulation provided in Table 1 is stated as the weight (mg) of each component per tablet.

TABLE 1

| Components | Mg/tab |
| --- | --- |
| Vitamin A and D beadlets | 13.0 |
| Ascorbic Acid | 103.0 |
| Matrix with embedded lubricant (vitamin E) | 0-142.8 |
| Niacinamide | 20.1 |
| Calcium Pantothenate | 11.1 |
| Dicalcium Phosphate Anhydrous | 467.7 |
| Calcium Carbonate | 160.9 |
| Copper (II) Sulfate | 4.9 |
| Ferrous Fumarate | 55.8 |
| Magnesium Oxide | 168.9 |
| Manganese (II) Sulfate Monohydrate | 7.4 |
| Potassium Chloride | 151.1 |
| Silicon Dioxide | 4.0 |
| Zinc Oxide | 14.4 |
| Mixed carotinoids | 25.8 |
| Mixed trace minerals | 8.0 |

TABLE 1-continued

| Components | Mg/tab |
|---|---|
| Mixed B vitamins | 1.7 |
| Microcrystalline cellulose | 141.1 |
| Crospovidone | 14.0 |

The above ingredients were passed through a No. 20 (U.S. Standard Mesh) hand screen, and blended together using a V-blender in a single step. All samples were mixed identically except for the amount of matrix with embedded lubricant added. The resulting compression mixtures with various concentrations of the matrix with embedded lubricant (Vitamin E) were paddle-fed into the dies for compression using a Manesty Beta Press and modified oval shape tablet tooling. Compression forces were targeted at 30, 40, and 50 kN, with a pre-compression force of about 8 kN and press speed at 85 rpm. The tablets were 0.330 inch wide, 0.745 inch long and approximately 0.280 inch thick (with slight variation in size do to the varying amounts of matrix with embedded lubricant used). The Manesty Betapress was instrumented to monitor both compression force and ejection force, and recorded results using MCC software. Tablets were evaluated for hardness by Hardness Tester (Dr. Schleuniger Pharmatron, Model 6D-500N), friability by Vanderkamp Friabilator (Van-Kel Industry, Model 10809), weight by Analytical Balance and thickness by Caliper. The Vitamin E matrix performed well as the sole lubricant with minimal impact on tablet hardness, friability, and disintegration time (DT).

The compression mixtures were found to be well lubricated for compression and subsequent ejection from the dies with a minimum of 0.3% matrix with embedded Vitamin E by weight (or 0.15% Vitamin E), and smooth surfaced and elegant in appearance with a minimum of 1.2% Matrix with embedded Vitamin E (or 0.6% Vitamin E). 0.3% of matrix with embedded Vitamin E was sufficient for providing equivalent ejection forces as a comparable vitamin and mineral supplement in which 0.3% Magnesium stearate is used as the lubricant.

The addition of matrix with embedded Vitamin E generally lowered tablet hardness with increasing concentration at any one of three fixed compression forces (30, 40 and 50 kN). The decrease in hardness at the compression forces tested was not as large as the changes over the same range of compression forces for a comparable vitamin and mineral composition using Magnesium stearate as a lubricant (e.g. the presence of 0.3% Magnesium stearate lowered tablet hardness by 5 kP compared to no significant lowering effect on tablet hardness by 0.3% of matrix with embedded Vitamin E over the range of compression forces tested). The matrix with embedded Vitamin E was found to decrease the friability by approximately 50% at all concentrations tested (0.3-8.8%) as compared to a comparable tablet composition differing only in the use of magnesium stearate as a tableting lubricant. The presence of matrix with embedded Vitamin E at low concentrations (0-1.2%) did not show significant impact on disintegration times, however, increased the disintegration times from 0.9 to 2 and 4 min at higher concentrations (2.4% and 4.6%). It is well know in the art that for vitamin and mineral compositions addition magnesium stearate even at low concentrations (ca. 0.3%) usually increases disintegration times due to the hydrophobic nature it imparts on the compression blend.

The matrix with embedded Vitamin E was also found to be compatible with other ingredients in vitamin and mineral tablets. The Vitamin E was fully recoverable and stable after compressed into tablets based on an accelerated stability study. No significant impacts of the Matrix with embedded Vitamin E were observed on the stability of other ingredients in vitamin and mineral tablets.

Compression of vitamin and mineral composition with 4.6% Matrix with embedded Vitamin E was scaled up to a commercial rate up to 5500 tablets per minute on a high-speed commercial double-sided rotary press. Each punch and die set produced approximately 90 tablets per minute. The tablets were found to be smooth surfaced and elegant in appearance. The matrix with embedded Vitamin E appeared to effectively lubricate the compression blend for compression at normal commercial production rates.

Example 3

Possible effects of over-mixing on compressibility of a multivitamin and mineral composition with Matrix with embedded Vitamin E as the lubricant were investigated. The over-mixing experiments were performed in an 8 L Littleford Granulator at 400 rpm. Unlike the V-blender's tumble mechanism of mixing, this apparatus uses plow blades at a high rpm. A sample of multivitamin and mineral composition with 4.6% Matrix with embedded Vitamin E was prepared and compressed after mixed in the Littleford for 0, 2, 4, 10 and 20 minutes. The extent of mixing had no significant impact on tablet hardness, and friability, but slightly decreased the ejection force for tablets of the composition lubricated with the matrix with embedded Vitamin E. For comparison, a vitamin and mineral composition with 0.3% Magnesium stearate in place of the matrix with embedded Vitamin E but alike in all other respects was also prepared and compressed after mixed in the Littleford for 0, 2, 4, 10, and 20 minutes. Increasing the mixing time significantly reduced tablet hardness, slightly decreased ejection force, and significantly increased friability for tablets of using 0.3% magnesium stearate as a lubricant. Table 2 shows exemplary data for tablet hardness for tablets compressed at 40 kN after 0, 2, 4, 10 and 20 minutes of mixing.

TABLE 2

TABLE OF COMPARISON DATA FOR OVER MIXING

| Blending Time (min) | Hardness (kP) for the multi Vit/Mineral formulation with Mg Stearate as lubricant | Hardness (kP) for the multi Vit/Mineral formulation with Vit E as lubricant |
|---|---|---|
| 0 | 27.2 | 31.7 |
| 2 | 24.9 | 30.4 |
| 4 | 21.0 | 31.5 |
| 10 | 16.9 | 30.8 |
| 20 | "Too soft to measure with available equipment" | 31.8 |

As the data of Table 2 shows mixing time had little effect on the hardness of tablets lubricated with the matrix with embedded Vitamin E, but the hardness of tablets with 0.3% Magnesium stearate was very sensitive to mixing time.

Although the foregoing invention has been described in some detail by way of illustration and examples for purposes of clarity of understanding it will be obvious that certain changes and modifications may be practiced within the scope of the appended claims. Modification of the above-described modes of practicing the invention that are obvious to persons of skill or the art are intended to be included within the scope of the following claims.

What is claimed is:

1. A nutritional supplement tablet composition comprising 0.1% to 1.5% weight/weight of an embedded lubrication matrix, wherein the embedded lubrication matrix comprises Vitamin E oil finely dispersed in an oil insoluble material and interspersed in interstitial spaces of the oil insoluble material, wherein the oil-insoluble material does not assemble a layer over the surface of the Vitamin E oil, and wherein the nutritional supplement composition comprises less than 0.01% stearate by weight.

2. The nutritional supplement tablet composition of claim 1, wherein the oil-insoluble material is selected from the group consisting of starch, dextrin, microcrystalline cellulose, ethylcellulose, gelatin, glucose, maltose, fructose, sorbitol, sucrose, mannitol, sorbitol, lactose, methylcellulose, hydroxypropylmethyl cellulose, maltodextrin, silicon dioxide, anhydrous dicalcium phosphate, and combinations thereof.

3. The nutritional supplement tablet composition of claim 1, wherein the composition further comprises at least one mineral.

4. The nutritional supplement tablet composition of claim 1, wherein the composition further comprises at least one vitamin.

5. The nutritional supplement composition of claim 1, wherein the composition further comprises at least one nutritional agent.

6. The nutritional supplement tablet composition of claim 5, wherein the at least one nutritional agent is selected from the group consisting of carotenoids, fiber, phytosterols, glucosides, polyphenols, B complex related compounds, omega-3 fatty acids, probiotics, glucosamine, amino acids, peptides, and combinations thereof.

7. The nutritional supplement tablet composition of claim 1, further composing at least one vitamin and at least one mineral.

8. The nutritional supplement tablet composition of claim 1, wherein the composition is a direct compression composition.

9. The nutritional supplement tablet composition of claim 1, wherein the composition comprises a granulation.

10. A multivitamin and mineral composition comprising 0.1% to 1.5% weight/weight of an embedded lubrication matrix wherein the embedded lubrication matrix comprises Vitamin E oil finely dispersed in an oil insoluble material and interspersed in interstitial spaces of the oil insoluble material, wherein the oil-insoluble material does not assemble a layer over the surface of the Vitamin E oil, and wherein the nutritional supplement composition comprises less than 0.01% stearate by weight.

11. The multivitamin and mineral composition of claim 10, wherein the oil-insoluble material is selected from the group consisting of starch, dextrin, microcrystalline cellulose, ethylcellulose, gelatin, glucose, maltose, fructose, sorbitol, sucrose, mannitol, sorbitol, lactose, methylcellulose, hydroxypropylmethyl cellulose, maltodextrin, silicon dioxide, anhydrous dicalcium phosphate, and combinations thereof.

12. The multivitamin and mineral composition of claim 10, wherein the composition further comprises at least one nutritional agent.

13. The multivitamin and mineral composition of claim 12, wherein the at least one nutritional agent is selected from the group consisting of carotenoids, fiber, phytosterols, glucosides, polyphenols, B complex related compounds, omega-3 fatty acids, probiotics, glucosamine, amino acids, peptides, and combinations thereof.

14. The multivitamin and mineral composition of claim 10, wherein the composition is a direct compression composition.

15. The multivitamin and mineral composition of claim 10, wherein the composition comprises a granulation.

16. A method of lubricating a nutritional supplement composition comprising providing the embedded lubrication matrix of claim 1, providing a nutritional supplement composition, mixing the embedded lubrication matrix and the nutritional supplement composition, and forming a tablet, wherein the nutritional supplement composition is substantially free of stearate.

* * * * *